United States Patent [19]

Vincent et al.

[11] Patent Number: 5,007,935
[45] Date of Patent: Apr. 16, 1991

[54] JOINT MEMBER FOR A HIP PROSTHESIS

[75] Inventors: Andre Vincent, La Hulpe; Evrard Munting, Brussels, both of Belgium

[73] Assignee: S. A. Manufacture Belge De Gembloux, Gembloux, Belgium

[21] Appl. No.: 352,643

[22] Filed: May 12, 1989

Related U.S. Application Data

[63] Continuation of Ser. No. 929,192, Sep. 10, 1986, abandoned.

[51] Int. Cl.$^5$ .............................................. A61F 2/32
[52] U.S. Cl. ...................................................... 623/22
[58] Field of Search ...................... 623/16, 18, 20, 21, 623/22, 23

[56] References Cited

U.S. PATENT DOCUMENTS

| | | | |
|---|---|---|---|
| 2,397,545 | 4/1946 | Hardinge | 128/92 YV |
| 2,612,159 | 9/1952 | Collison | 128/92 YV |
| 3,053,251 | 9/1962 | Black et al. | 623/23 |
| 4,005,495 | 2/1977 | Locke et al. | 623/23 X |
| 4,129,903 | 12/1978 | Huggler | 623/23 |
| 4,195,366 | 4/1980 | Jarcho et al. | 623/16 |
| 4,312,079 | 1/1982 | Dörre et al. | 623/23 |
| 4,673,407 | 6/1987 | Martin | 623/20 |

FOREIGN PATENT DOCUMENTS

| | | | |
|---|---|---|---|
| 0099167 | 1/1984 | European Pat. Off. | |
| 2659591 | 7/1977 | Fed. Rep. of Germany | 623/16 |
| 2827529 | 1/1980 | Fed. Rep. of Germany | 623/16 |
| 3216538 | 11/1983 | Fed. Rep. of Germany | 623/22 |
| 2475891 | 8/1981 | France | 623/22 |
| 0101145 | 6/1984 | Japan | 623/16 |
| 764438 | 12/1956 | United Kingdom | 623/22 |

Primary Examiner—David J. Isabella
Attorney, Agent, or Firm—Kinney & Lange

[57] ABSTRACT

Joint member for a hip prosthesis having a joint head, a supporting portion including a supporting surface cooperating with a corresponding supporting surface on the proximal femur and fixation means members for securing joint head and supporting means portion to the femur, characterized in that a shankless and block-like supporting member (4, 41) includes at least a supporting surface (10, 11, 43, 44) disposed adjacent the joint head (2, 40) such that the corresponding femur supporting surface (7", 7') is adjacent the proximal medical femoral cortex, in that further retaining means members (15, 21) are provided coacting with the proximal femur (7) and engaging the supporting member (4) through a bore (13') in the femur supporting surface (7") in order to exert a tensile force on the supporting member (4) laterally to press the supporting surface (10, 11) against the femur supporting surface (7", 7'), and in that the supporting member (4) and/or the retaining members are prevented from rotation about the axis of the femur neck.

21 Claims, 3 Drawing Sheets

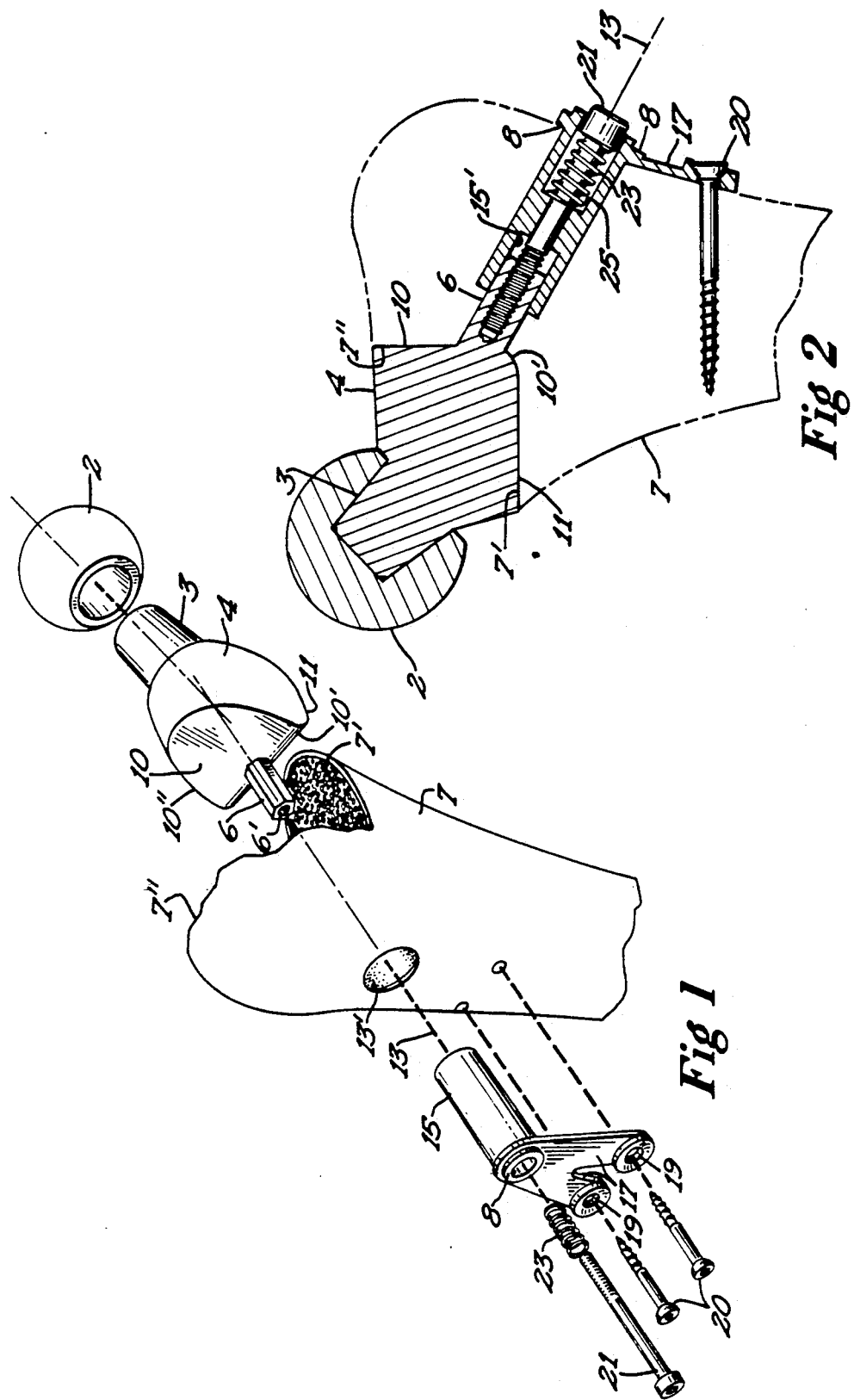

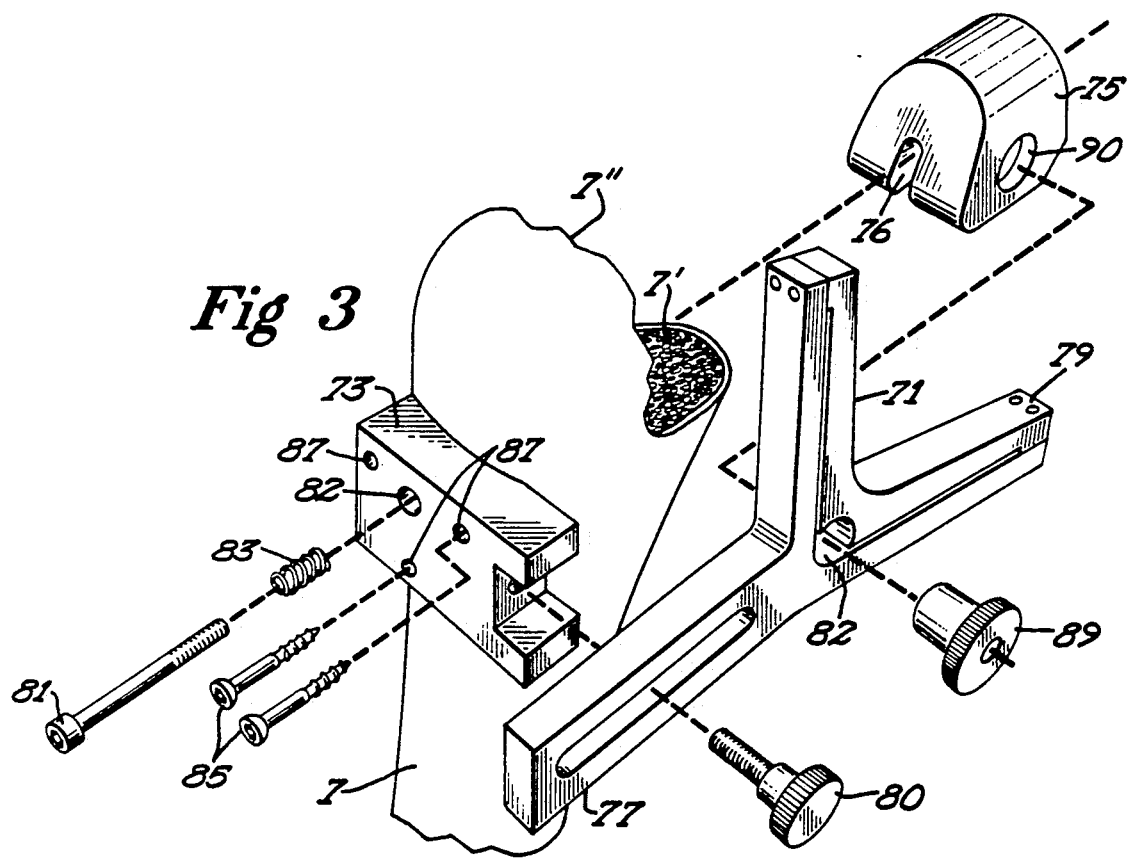
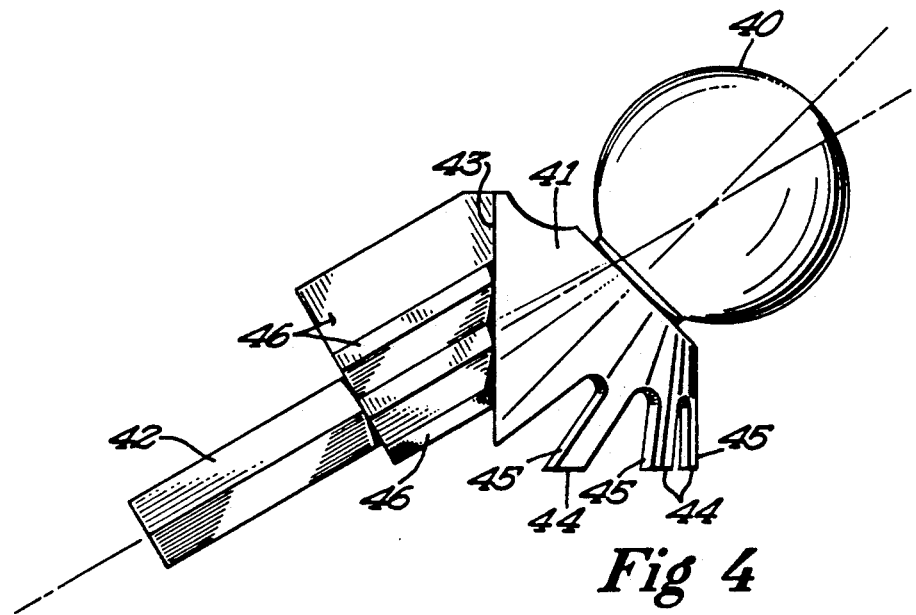

JOINT MEMBER FOR A HIP PROSTHESIS

This is a Continuation of application Ser. No. 06/929,192, filed Sept. 10, 1986 (now abandoned).

BACKGROUND OF THE INVENTION

In femoral joint members of conventional hip prostheses the joint head is connected via a joint neck to a shank adapted to be introduced in the medullary canal of the femur. The elongated shank which is wedge-like in the lateral-medial plane is either secured in the femur by a jamming effect and/or by means of bone cement. In both cases the medullary canal has to be prepared by a drilling operation in order to allow the insertion of the shank. A flange-like collar between the prosthesis neck and the shank engages a corresponding surface of the proximal femur and serves for the support of the prosthesis. The force transfer from the joint head of the prosthesis to the femur substantially takes place through the prosthesis shank.

Follow-up studies brought about that after a period of ten years after the implantation the loosening rate reaches 35% of the patients operated. Patients operated on before the age of 30 years sustain a loosening of up to 57% within the five years following the implantation. Loosened prostheses cause pain and require hazardous reoperations.

The main reason for the loosening of the prostheses is seen in the different modulus of elasticity of the bone material and the prosthesis shank, respectively. Due to oscillating loads so-called micro movements occur in the prosthesis shaft leading to a micro-fatigue fracture at the interface of both materials.

The stress pattern of the normal femur changes by the implantation of a prosthesis Portions of the femur normally allowing extreme loads are not loaded in the same amount after a prosthesis has been implanted. Consequently a remodeling of the bone structure happens which also contributes to a loosening of the prosthesis. Additionally, the drilling operation for the insertion of the shank considerably weakens the portions above the proximal medial femoral cortex which normally has a high load capacity.

Attempts have been made to obviate the mentioned problems by allowing an ingrowth of bone material in corresponding parts of the prosthesis. For this purpose the surface of the prosthesis is provided with irregularities, openings or the like or by developing a bone cement such that it allows an ingrowth of the bone material. These attempts are not completely satisfactory.

SUMMARY OF THE INVENTION

The invention is based on the problem to provide a hip prosthesis which allows an appropriate introduction of force into the femur and which does not lead to a loosening after a long period of time and which does not lead to undesired deformation of the femur.

The joint member according to the invention includes a block-type supporting member. A prosthesis shank as usual with conventional femoral prostheses is not provided. The block-type shankless supporting member includes at least one supporting surface which is located adjacent to or a small distance from the joint head such that the corresponding femur supporting surface is positioned adjacent the proximal medial femural cortex. By means of suitable retaining means which coact with the supporting member through a bore in the femur-supporting surface the supporting member is fixedly drawn or pressed against the femur-supporting surface. The retaining means is not provided for bearing the load to which the joint head is subjected, rather, it serves substantially the purpose of pressing the support member fixdely against the supporting surface of the femur. The transfer of force from the joint head to the femur is intended to take place immediately through the supporting surface(s). Suitable means on the supporting member or on the retaining means prevent a rotation of the supporting member approximately about the axis of the femur neck. Above all, after the operation, when the supporting member and the femur are not grown together there is a danger that the supporting member rotates or tilts. Retaining means and antirotation means prevent a tilting and rotating without substantially contributing to the introduction of force into the femur.

The retaining or fastening means thus, above all, serves for the primary supply after the replacement of the hip joint. After supporting member and femur have grown together the retaining means can be removed if desired.

An antirotational effect for the supporting member can be achieved in that the supporting member and the retaining means are provided with co-operating surfaces which prevent rotation of the supporting member. Additionally or alternatively the supporting surface on the supporting member can be oriented such that a torsion or rotational force on the supporting member about approximately the axis of the femur neck results in a component normal to the femur supporting surface. With such a supporting surface on the supporting member a rotational force thereon would lead to a spreading of the supporting surfaces of the supporting member and the femur. This would cause considerable forces which are effective as counter-forces relative to the rotational forces possibly effective on the supporting member.

It is preferred to have first and second supporting surfaces on the supporting member which includes an angle between each other, preferably a right angle. One supporting surface extends approximately perpendicularly to the femur axis while the other extends approximately in parallel to the femur axis. During the operation a corresponding V-shaped cut is made in the proximal femur. The complementarily formed supporting member is positively inserted in the cut. The supporting surface extending substantially parallel to the femur axis preferably has a length in this direction which is of ⅔ of the length of the extension of the supporting surface transverse to the femur axis. It is not necessary that the mentioned supporting surfaces are plane, rather, they could be composed of subsurfaces which include angles between them. Further, the supporting surfaces can be provided with elevations, indentations, recesses or the like for the ingrowth of bone material. It is particularly preferred if the supporting surface is defined by the end faces of a plurality of spaced webs, ribs or the like. Such ribs or webs are preferably formed in the portion of the supporting surface from which the force is transferred approximately in the axial direction to the femur. Such supporting webs or supporting ribs have two main functions. One relies on the fact that during the healing process a sufficient amount of bone substance can grow between the webs in order to achieve an intimate connection of the support member with the femur in order to allow the transfer of all forces from the joint head to femur. The second function is defined by a certain resiliency of the webs. Thus, no rigid prosthesis portion borders any much more resilient bone portions. Rather, in this region an adaptation of the resiliencies can be achieved so that the above mentioned fatigue phenomena will not occur. The webs, ribs or the like can be provided with toothings, grooves, holes or the like in order to facilitate the ingrowth of the bone material.

In one embodiment of the invention an extension is provided below the supporting surface of the supporting member, the extension coacting with the retaining means. The extension may include an angle of 30° to 45° to one of the supporting surfaces which include a right angle therebetween. The extension is engaged by the retaining means in order to press the supporting member laterally as described above. The extension is inserted in the femur and can be provided with further means to facilitate an ingrowth of bone material and to achieve an anti-rotational effect. For this purpose a plurality of circumferentially spaced wings or fins can be formed at the extension, the radial ends of the wings being disposed radially inwardly of the associated edge of the supporting surface.

Different suitable retaining means can be used in order to secure the prosthesis according to the invention to the proximal femur. A preferred embodiment provides tensional anchoring means engaging the supporting member, an opposite surface of the anchoring means cooperating with the lateral surface of the proximal femur. The tensional anchoring means may include a screw bolt which can be threaded into a threaded bore of the supporting member and which is slidably guided in a sleeve, a compression spring being located between the head of the screw bolt and the sleeve. Such an arrangement resembles the so-called "Pohl'sche Lasche" which-enables an osteosynthesis of femur neck fractures. By the way it is known to secure a prosthesis head to the femur by such tensional anchoring means. In the known prosthesis a flange is provided at one end of the prosthesis neck which is seating against a respective supporting surface of the femur. In such a prosthesis the main forces are introduced into the femur through the anchoring means. Such force transfer is leading to high surface pressures which also could result in a loosening of the prosthesis. Furthermore, the known prostheses have no means for preventing a rotation of the prosthesis head which may also lead to a loosening. In the invention the tensional anchoring means essentially serves only for a pressing of the supporting member against the femur and do not—or only to a minor extent—contribute to an introduction of force into the femur.

A further anti-rotational effect can be achieved by the mentioned extension being provided with a section having a polygonal cross section, the polygonal section being adapted to be inserted in a complementary socket section of the sleeve of the anchoring means. In this case means have to be provided preventing a rotation of the sleeve.

It is preferred to form the prosthesis of the invention of pure titanium which is particularly biologically compatible to the human body.

The invention will be explained hereinafter by way of some drawings.

BRIEF DESCRIPTION OF THE DRAWINGS

FIG. 1 is a schematic perspective exploded view of a first embodiment of the invention.

FIG. 2 shows a section through the prosthesis according to FIG. 1 in its implanted state.

FIG. 3 is an exploded view showing the preparation of the femur in order implant the prosthesis according to the invention.

FIG. 4 is a side view of another embodiment of the invention.

DETAILED DESCRIPTION OF THE DRAWINGS

Figure 5:
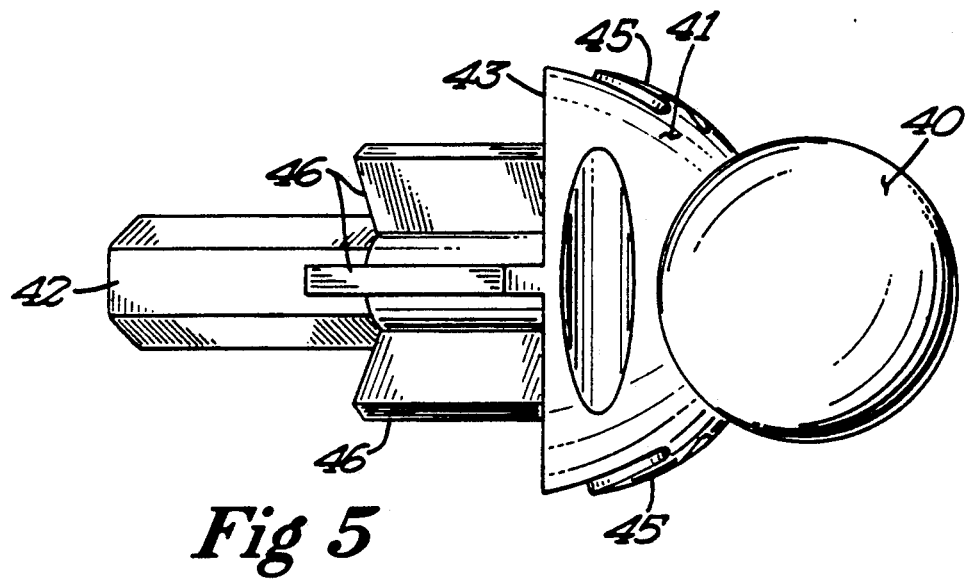
FIG. 5 shows a top plan view of the prosthesis according to FIG. 4.

Before going into detail it should be mentioned that each feature to be described may be a part of the invention per se or in connection with the features of the claims.

FIGS. 1 to 3 show the proximal portion 7 of a femur which has been provided with a rectangular cut in a manner as to be described later. By the cut a supporting surface 7' is formed extending substantially rectangularly to the femur axis. A further vertical supporting surface 7" is formed extending approximately parallel to the femur axis. The femur 7 is provided with a through-bore 13' along an axis 13 extending at a small acute angle to the natural femur neck axis.

The femoral prosthesis illustrated in FIGS. 1 and 2 comprise a block-like supporting member 4 including a medially extending conical plug 3 which co-operates with the conical bore in a joint ball 2. The supporting member 4 includes two supporting surfaces 10, 11 including a right angle therebetween, the intersection line of the supporting surfaces 10, 11 being rounded as shown at 10'. Near the rounded edge 10' an extension 6 extends from the supporting surface 10 along the axis 13, the extension 6 having a hexagonal cross section. The extension 6 includes a threaded axial bore 6'. The supporting surfaces 10 and 11 are defined by the rounded edge 10' and an arcuate edge 10". This can be seen in FIG. 2 relative to the supporting surface 10. The supporting surface 11 is formed correspondingly. The supporting member 4 has a rounded external contour between the supporting surfaces 10, 11.

As can be seen in FIG. 2, the supporting member 4 is matched to the cut of femur 7 said cut being defined by the supporting surfaces 7', 7". As can be seen in FIG. 2 further the length of the supporting surface 10 if viewed in axial direction is ⅔ of the length of the supporting surface 11 if viewed transverse to the femur axis. If the supporting member 4 is inserted in the mentioned cut, the extension 6 is introduced into the bore 13'. A sleeve 15 is introduced into the bore 13' laterally, the sleeve including a socket portion 15' at its interior end portion, the socket portion having a hexagonal cross section. The cross section of the socket portion 15' is such that the extension 6 is matching the socket portion 15'. A screw bolt 21 is introduced in the sleeve 15, the screw bolt 21 being threaded in the threaded bore of the extension 6. A spring 23 is located in an enlargement 25 of the sleeve bore, one end of the spring 23 is seated against the shoulder of the enlargement, the other end of the spring seating against the lower side of the bolt head. Since the bolt head also is slidingly received by the sleeve the supporting member 4 can move away from the supporting surfaces 7', 7" a small amount if engaged by the respective forces. A flange 8 is formed on the lateral side of the sleeve 15, the flange engaging the lateral side of the femur 7. Plate-like extensions 17 are integrally formed with the flange, the extensions 17 being disposed in a bifurcate arrangement and including holes 19 at the ends thereof which receive bone screws 20. The relay, the extension 17 can be fixedly secured to the femur 7 by the bone screws and thus prevent rotation of the sleeve 15.

As can be particularly seen in FIG. 2 the introduction of force from the prosthesis head into the femur 7 takes place essentially through the supporting surfaces 10, 11 and the supporting surfaces 7', 7", respectively. The femur supporting surface 7' substantially receives the compression forces in the region of the proximal medial femural cortex, while the femur supporting surface 7" substantially receives the smaller tensional forces. A portion of the tensional forces is also received by the extension 6 and the anchoring means as shown. The anchoring means as shown by which the supporting member 4 is pressed against the supporting surfaces 7', 7" of the femur is important above all for a primary supply before the supporting member and the femur are grown together. To enhance this effect, the supporting member can be provided with holes, elevations, toothings, indentations or the like. The engagement of the extension 6 with the sleeve 15 contributes to the rotational stability of the supporting member 4 together with the specific orientation of the supporting surfaces 10, 11. As can be seen, supporting member 4, extension 6 and tap 3 are integrally formed, e.g. by casting. Preferably pure titanium is used.

Figure 6:
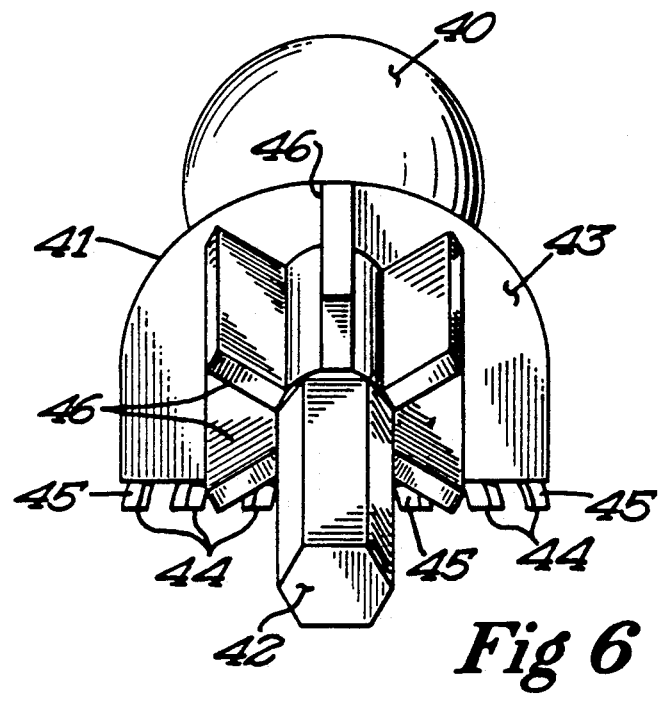
FIG. 6 is a posterior view of the prosthesis according to FIG. 4.

The prosthesis member shown in the FIGS. 4 to 6 comprises a joint ball 40, a supporting member 41 and a hexagonal extension 42. The hexagonal extension 42 is integrally formed with the supporting member 41 and resembles the extension 6 of the embodiment described above. The supporting member 41 includes a supporting surface 43 substantially parallel to the femur axis. A further supporting surface 44 extending perpendicularly to the supporting surface 43 is defined by the plane end surfaces of webs 45 which extend downwards from the solid portion of the supporting member 41 substantially normal to the common plane of the end faces. The external edges of the webs 45 are arranged on an arc (see FIG. 4 in connection with FIG. 6). The axis of the webs parallel to the common plane extends radially to the arc so that the distances between the webs radially inwards are smaller than radially outwards. The surfaces of the webs facing each other are provided with a toothing or with grooves which is not illustrated. The webs further can be provided with holes or the like which is also not shown. As can be seen in FIG. 6 the contour of the supporting surface 43 resembles the contour of the supporting surface 10 of the supporting member 4 according to FIGS. 1 and 2. Wings 46 or fins extend from the supporting surface 43, the wings 46 being radially formed at the extension 42. In this embodiment as shown six wings 46 are equally circumferentially spaced. The wings 46 also can be provided with holes, recesses, toothings or the like also at their end faces. Upon implantation the wings are introduced in a corresponding bore in the femur along the axis 13 of FIG. 1.

The implantation of the prosthesis shown in FIGS. 4 to 6 is similar to that of the prosthesis according to FIGS. 1 and 2. The main difference between the embodiments shown is that in the case of the supporting member 41 the support on the femur supporting surface 7' occurs through "legs" and not through a continuous plane supporting surface 11 according to FIG. 2. The spaces between the webs 45 or the legs enable an ingrowth of bone material during the healing process. The webs 45 further show a larger resiliency than a rigid supporting body. Bone material can also grow between the wings 46 and improve the secure fixation and the rotational stability of the prosthesis as shown. The prosthesis as shown according to FIGS. 4 to 6 enables also an intimate ingrowth of the femur bone such that the retaining means as shown in FIG. 2 will be only necessary for the first healing phase, afterwards the retaining means could be removed if desired.

The prosthesis shown in FIGS. 4 to 6 is also made preferably of titanium. The surfaces of the prosthesis contacting the bone can be coated with a material which improves the mechanical stability and enhances the ingrowth of bone material. Such a material is for instance tricalcum phosphate ceramic. The porous ceramic has a porosity of for instance 200 to 500 microns. The mentioned ceramic is resorbable, the resorbed ceramic will be slowly displaced by the bone substance.

In FIG. 3 tools are shown which serve for the implantation of the prosthesis according to FIGS. 1 and 2 or 4 to 6. In FIG. 3 an Y-like saw guide 71 is shown, the shaft 77 thereof includes a longitudinal slot for a screw 80 for an attachment to a bore gauge for bone screws 85 corresponding to bone screws 20 of FIG. 1, and for a screw bolt 81 corresponding to the screw bolt 21 which co-operates with a spring 43 corresponding to spring 23 of Fing 1. In the arms of the guide 71 slots are provided forming a right angle. At the intersection of the arms a bore 82 is formed. By means of the slots in the arms 29 the supporting surfaces 7', 7" are cut in the femur 7. The radius at the intersection line of the supporting surfaces is made by a drilling tool introduced through the bore 82. Thereafter a template 75 for the throughbore 76 is placed in the cut thus formed, the lateral recess thereof co-operating with the shaft of the screw 89 placed in the recess 90 through the bore 82. In this way the bore 13' in femur 7 (see FIG. 1) is formed.

We claim:

1. A stemless femoral prosthesis comprising:
    a block shaped supporting member configured to be positioned on a V-shape resected surface in the medial surface at the proximal end of the femur;
    a joint head connected to the supporting member;
    an anti-rotation means extending outwardly from the supporting member;
    a retaining means to be positioned on the lateral surface of the femur and operatively coupled to the anti-rotation means to exert a tensile force on the supporting member thereby urging the supporting member against the resected surfaces; and
    said supporting member including supporting surfaces designed to cooperate with the V-shaped resected surface of the bone, one of the supporting surfaces positioned generally parallel to the femur axis and another of said supporting surfaces positioned essentially perpendicular thereto.

2. The femur hip prosthesis according to claim 1, characterized in that said supporting surfaces include irregularities allowing ingrowth of bone material.

3. The femoral hip prosthesis according to claim 1, characterized in that the supporting surfaces are joined at a rounded edge, each supporting surface further defined by an arcuately-shaped edge to define a rounded external contour for the supporting member.

4. The femoral hip prosthesis according to claim 1, including a plurality of webs extending from at least one of the supporting surfaces to defined a series of further supporting surfaces positioned some distance from, but parallel to the supporting surface.

5. The femoral hip prosthesis according to claim 4, characterized in that the webs are circumferentially placed about the arcuately-shaped edge of said support surface.

6. The femoral hip prosthesis according to claim 4, characterized in that the web surfaces are formed with irregularities to promote bone ingrowth.

7. The femoral hip prosthesis according to claim 1, characterized in that the anti-rotation means is an extension designed to cooperate with the retaining means.

8. The femoral hip prosthesis according to claim 7, characterized in that a plurality of radial wings are formed to the extension.

9. The femoral hip prosthesis according to claim 1, characterized in that the retaining means includes an anchoring means engaging the supporting member and a portion of the lateral surface of the femur.

10. The femoral hip prosthesis according to claim 7, characterized in that the retaining means includes a sleeve disposed through a throughbore in the femur aligned with the femur neck axis, the sleeve including a socket portion configured to receive the extension therein.

11. The femoral hip prosthesis according to claim 10, characterized in that the extension has a polygonal shaped crosssection adapted for insertion into a polygonal shaped socket, the polygonal shape serving to inhibit the rotational movement of the extension within the socket.

12. The femoral hip prosthesis according to claim 10, characterized in that a screw bolt is inserted through the sleeve and adapted for connection with a threaded axial bore of the extension.

13. The femoral hip prosthesis according to claim 12, characterized in that said retaining means further includes a spring seated against a lower side a head of the screw bolt whereby, the spring permits the adjustment of the support member in response to the application of certain forces.

14. The femoral hip prosthesis according to claim 10 characterized in that the sleeve includes a means for restricting the rotation of the sleeve within the throughbore about the femur neck axis.

15. The femoral hip prosthesis according to claim 1, characterized in that the retaining means includes a plate means operatively associated therewith, the plate means engaging a portion of the lateral surface of the femur to inhibit the rotational movement of the retaining means.

16. The femoral hip prosthesis according to claim 15, characterized in that the plate means is secured to the surface of the femur by a bone screw.

17. The femoral hip prosthesis according to claim 1, characterized in that at least one of the supporting surfaces is coated with a material that is at least partially resorbable.

18. The femoral hip prosthesis according to claim 17, characterized in that the resorbable material has pores of a diameter of about 200 to 500 micron.

19. The femoral hip prosthesis according to claim 1, characterized in that the supporting members are made of essentially pure titanium (99.99%).

20. The femoral hip prosthesis according to claim 1, characterized in that at least one of said supporting surfaces is non-planar.

21. The femoral hip prosthesis according to claim 1 characterized in that at least one of said supporting surfaces is defined by a series of subsurfaces which extend at an angle relative to each other.

* * * * *